(12) United States Patent
Smit et al.

(10) Patent No.: US 6,902,673 B2
(45) Date of Patent: Jun. 7, 2005

(54) SINGLE PORT MANIFOLD

(75) Inventors: Karen L. Smit, Kalamazoo, MI (US); Mark Wasserman, Delton, MI (US)

(73) Assignee: Stryker Instruments, Kalamazoo, MI (US)

(*) Notice: Subject to any disclaimer, the term of this patent is extended or adjusted under 35 U.S.C. 154(b) by 46 days.

(21) Appl. No.: 10/205,051

(22) Filed: Jul. 25, 2002

(65) Prior Publication Data

US 2004/0016691 A1 Jan. 29, 2004

(51) Int. Cl.$^7$ .............................................. B01D 29/05
(52) U.S. Cl. ........................ 210/335; 210/445; 210/455; 210/479; 210/482
(58) Field of Search ........................... 210/335, 416.1, 210/445, 455, 304, 477, 479, 482; 604/322, 406; 433/92; 406/322, 406

(56) References Cited

U.S. PATENT DOCUMENTS

| | | |
|---|---|---|
| 110,136 A | 12/1870 | Hemenway |
| 493,378 A | 3/1893 | Gibson |
| RE24,255 E | 12/1956 | Lund |
| 2,818,178 A * | 12/1957 | Hodsdon ................. 210/445 |
| 3,060,882 A | 10/1962 | Peters et al. |
| 3,085,689 A * | 4/1963 | Hering et al. .............. 210/232 |
| 3,295,686 A * | 1/1967 | Krueger ..................... 210/455 |
| 3,415,485 A | 12/1968 | Hirs et al. |
| RE27,399 E | 6/1972 | Urso |
| 4,141,379 A | 2/1979 | Manske |
| 4,322,054 A | 3/1982 | Campbell |
| 4,443,336 A | 4/1984 | Bennethum |
| 4,735,610 A | 4/1988 | Akkas et al. .............. 604/119 |
| 4,915,688 A | 4/1990 | Bischof |
| 5,251,664 A | 10/1993 | Arvidsson et al. |
| 5,308,483 A * | 5/1994 | Sklar et al. ................. 210/232 |
| 5,503,740 A * | 4/1996 | Callaghan et al. .......... 210/232 |
| 5,637,103 A | 6/1997 | Kerwin et al. ............. 604/317 |
| 5,914,047 A | 6/1999 | Griffiths ..................... 210/739 |
| 5,945,004 A | 8/1999 | Ohira et al. ................ 210/710 |
| 5,971,956 A | 10/1999 | Epstein ....................... 604/119 |
| 6,024,720 A | 2/2000 | Chandler et al. ............ 604/35 |
| 6,083,205 A | 7/2000 | Bourne et al. .............. 604/246 |
| 6,149,812 A | 11/2000 | Erickson ..................... 210/521 |
| 6,180,000 B1 | 1/2001 | Wilbur et al. ................ 210/85 |
| 6,244,311 B1 | 6/2001 | Hand et al. ................. 141/375 |
| 6,331,246 B1 | 12/2001 | Beckham et al. |
| 6,776,294 B2 * | 8/2004 | Lemonnier .................. 210/406 |

* cited by examiner

*Primary Examiner*—Matthew O. Savage
(74) *Attorney, Agent, or Firm*—Howard & Howard

(57) ABSTRACT

A manifold assembly (12) for a medical waste collection device (10) is provided. The manifold assembly (12) comprises a housing (14) and a cap (16) connected to the housing (14) by a snap-fit connection (18). The housing (14) includes a bottom (20) and a wall (24) extending upwardly therefrom about an axis (26). A support structure (22) is disposed on the bottom (20) of the housing (14) to support a plurality of filters (60, 62). The support structure (22) includes spaced inner (38) and outer (40) rings. The support structure (22) further includes a plurality of inner spokes (52) extending radially between the axis (26) and the inner ring (38) and a plurality of outer spokes (44) extending radially between the inner ring (38) and the outer ring (40). The rings (38, 40) and spokes (44, 52) have upper surfaces that are coplanar to define a filter support surface (30). The plurality of filters (60, 62) are supported by the filter support surface (30) to filter material from fluid entering the manifold assembly (12).

32 Claims, 4 Drawing Sheets

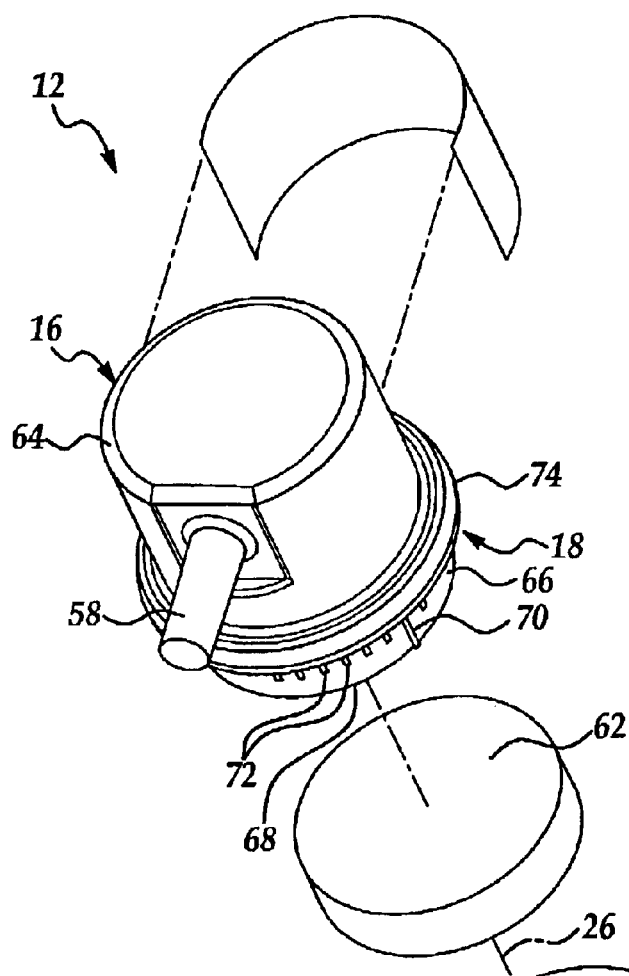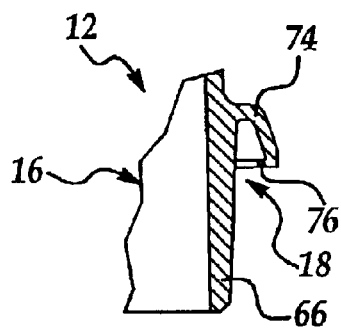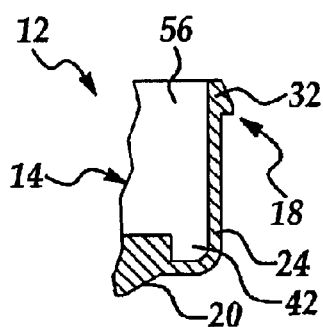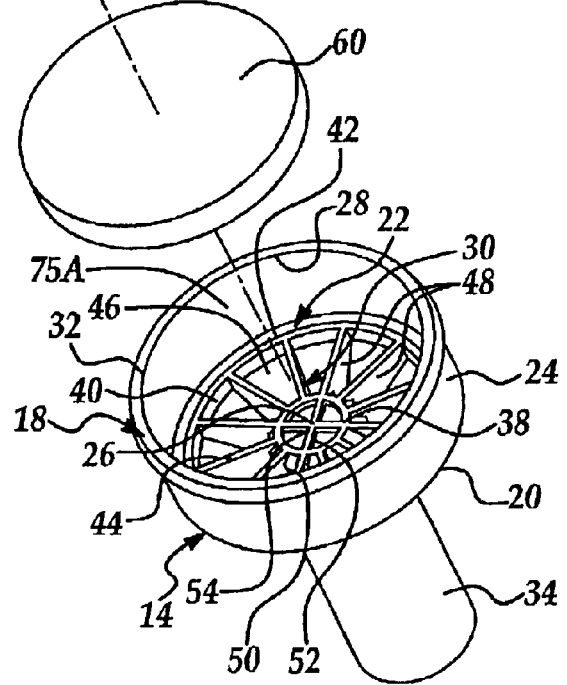
Figure 2
Figure 3
Figure 4

SINGLE PORT MANIFOLD

FIELD OF THE INVENTION

The subject invention relates generally to medical waste collection devices and, more particularly, to an assembly for filtering bodily fluids prior to being collected into the device.

BACKGROUND OF THE INVENTION

During many surgical procedures, waste materials are generated which must be captured and disposed of. Such waste materials include bodily fluids which have been drained from a patient or by-products that are produced, such as smoke from a cauterizing procedure.

Typically, a medical waste collection device having an intake manifold assembly in conjunction with a vacuum source is utilized to capture the waste materials, thereby reducing or eliminating the handling of such materials by employees and, in turn, reducing exposure of the employees to hazardous waste materials.

Each assembly generally includes a housing for storing the waste material, a lid having a vacuum port connected to the vacuum source, and a conduit extending between the patient and the manifold assembly through which the waste material travels. In operation, the vacuum source applies a negative pressure to the interior of the housing in order to pull the waste material from the patient through the conduit and into the intake manifold. Furthermore, a filter may be disposed in the assembly to prefilter the fluids or by-products prior to disposal.

Conventionally, such assemblies comprise many pieces, have a complex design, and are costly to manufacture and use. Such costs are passed on to the patient, thereby contributing to the high costs of health care.

The present invention is aimed at solving one or more of these disadvantages.

SUMMARY OF THE INVENTION AND ADVANTAGES

The subject invention provides a manifold assembly for use in a medical waste collection device. The assembly includes a manifold housing including a bottom with a support structure disposed thereon and a wall extending upwardly from the bottom about an axis to define an open periphery. The assembly further includes a manifold cap for disposition on the manifold housing for defining a chamber therebetween and a connection for connecting and retaining the housing and cap together. A support structure having a filter support surface is disposed above the bottom for defining a plurality of open spaces therein.

The manifold assembly of the present invention collects and filters waste materials produced during surgical procedures. The assembly is easily removed, disposed of, and replaced with another assembly, thereby reducing labor and cost. In addition, the assembly is easily manufactured and produced at a fraction of the cost of conventional manifold assemblies, in part due to the elimination of separate welding requirements.

BRIEF DESCRIPTION OF THE DRAWINGS

Other advantages of the present invention will be readily appreciated as the same becomes better understood by reference to the following detailed description when considered in connection with the accompanying drawings wherein:

FIG. 2 is an exploded perspective view of the manifold assembly according to one embodiment of the present invention;

FIG. 3 is a fragmentary cross-sectional side view of the brim on the cap of the assembly of FIG. 2;

FIG. 4 is a fragmentary cross-sectional side view of the shoulder on the housing of the assembly of FIG. 2.

DETAILED DESCRIPTION OF THE PREFERRED EMBODIMENT

Referring to the Figures, wherein like numerals indicate like or corresponding parts throughout the several views, a medical waste collection device is generally shown at 10 and includes a manifold assembly generally indicated at 12.

Figure 1:
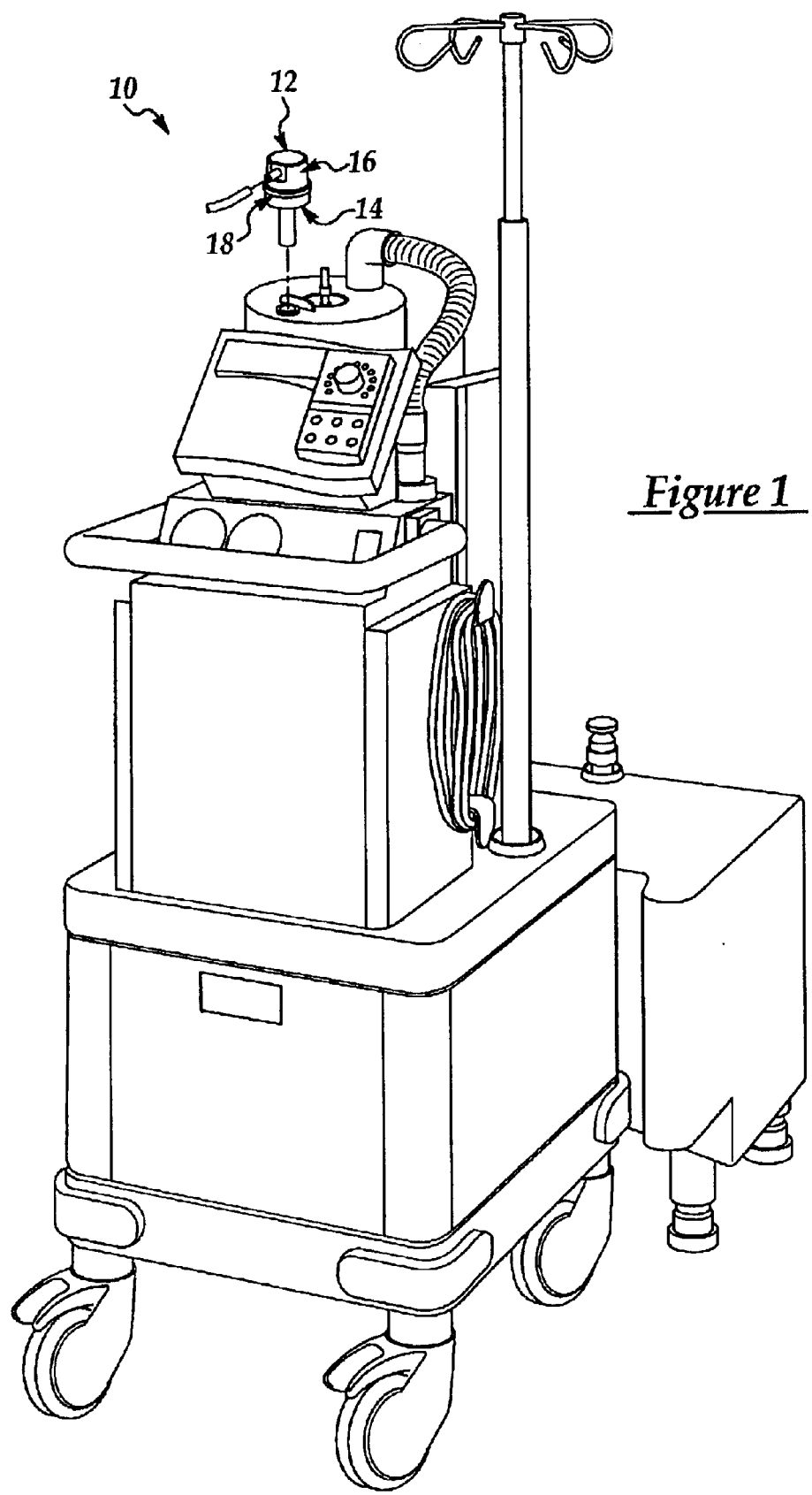
FIG. 1 is a perspective view of a waste collection device housing the manifold assembly according to one embodiment of the present invention.

The manifold assembly 12 includes a manifold housing, generally indicated at 14, a manifold cap, generally indicated at 16, and a connection, generally indicated at 18. As shown in FIG. 2, the manifold housing 14 and the manifold cap 16 are molded as two separate or single pieces that snap-fit together via the connection 18. As shown in FIG. 1, the assembly 12 is removably disposed on the device 10.

Figure 5:
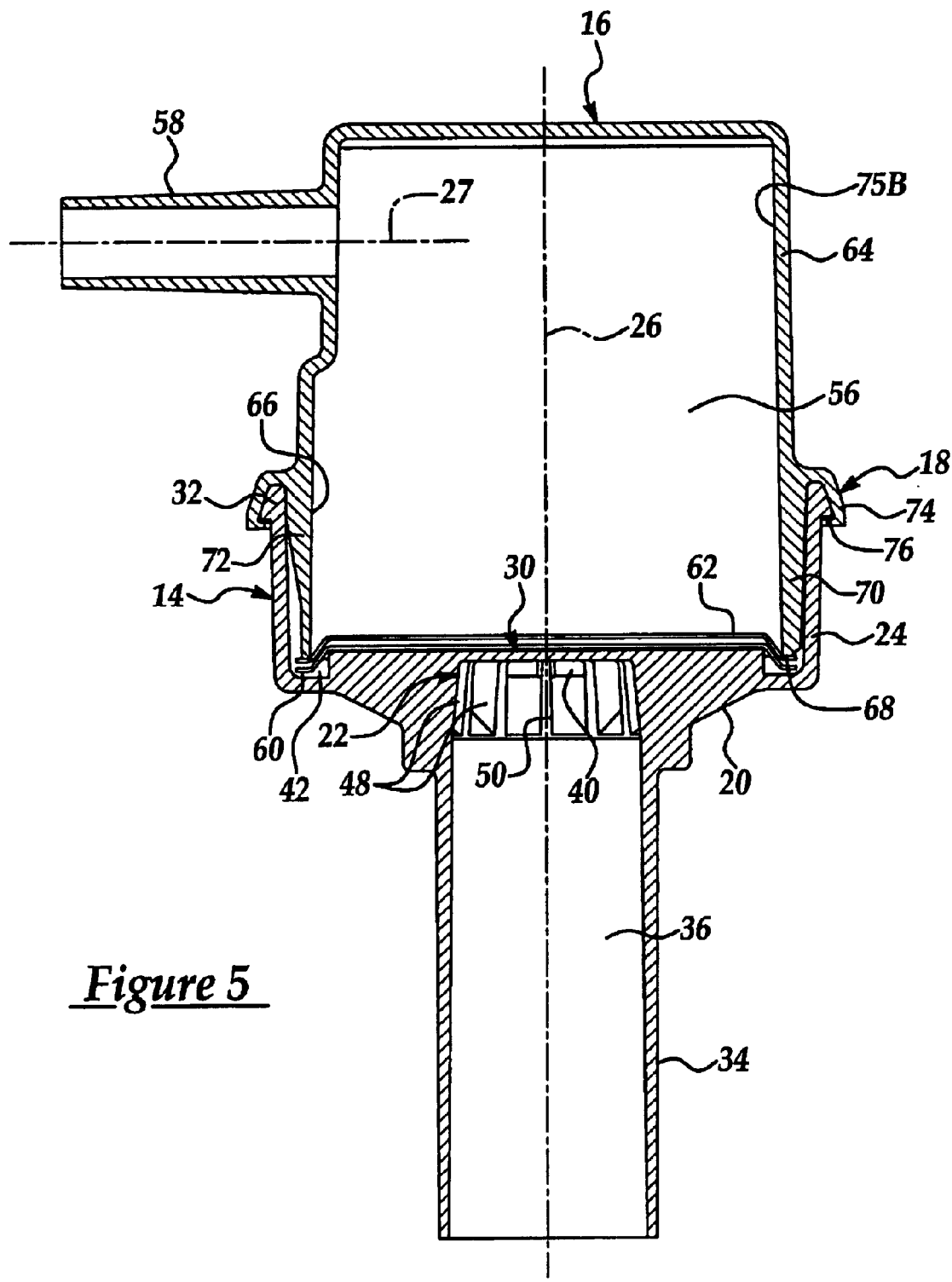
FIG. 5 is a cross-sectional side view of the assembled manifold assembly of FIG. 1.

The manifold housing 14 includes a bottom 20 with a support structure, generally indicated at 22, disposed thereon. A wall 24 extends upwardly from the bottom 20 about an axis 26 to define an open periphery 28. As shown in FIGS. 4 and 5, the support structure 22 defines a filter support surface, generally indicated at 30, above the bottom 20. A shoulder 32 is disposed about the exterior of the open periphery 28. An outlet port 34 is disposed on the bottom 20 and extends outwardly therefrom to define a passageway 36 extending into the bottom 20 for transporting waste to the device 10.

The filter support surface 30 includes an inner ring 38 and an outer ring 40. The inner ring 38 is disposed about and spaced from the axis 26. The outer ring 40 is spaced radially inwardly from the wall 24 to define a groove 42 between the outer ring 40 and the wall 24.

A plurality of outer spokes 44 extend radially between the inner and outer rings 38, 40 to define a plurality of open spaces 46 between adjacent spokes 44. Additionally, a plurality of inner spokes 52 extend radially between the axis 26 and the inner ring 38. The inner spokes 52 are diametrically aligned in pairs to define a cross 54 intersecting at the axis 26. Each of the pairs is aligned diametrically with a pair of the outer spokes 44.

As shown in FIG. 2, the support structure 22 and the bottom 20 are molded with the housing 14 as a one-piece structure. It is to be understood that the support structure 22 and the bottom 20 may each be molded as a separate piece which is mated with the housing 14.

The manifold cap 16 is disposed on the manifold housing 14 for defining a chamber 56 therebetween into which the passageway 36 extends. The cap 16 includes a top 64 and a skirt 66 unitary with and extending from the top 64 to a lower edge 68. The cap 16 further includes an intake port 58 disposed on the cap 16 about a second axis 27 transverse to the axis 26 for receiving waste materials generated during a surgical procedure which proceed into the chamber 56, through the passageway 36 and into the device 10. As shown in FIG. 1, the intake port 58 may be oriented on the cap 16 such that it is normal to the orientation of the outlet port 34 on the housing 14. However, it is to be understood that the intake port 58 may be disposed on the cap 16 such that it is oriented parallel with orientation of the outlet port 34 on the housing 14.

A primary filter 60 is disposed in the chamber 56 and is supported on the support structure 22 for filtering the waste materials and allowing waste to flow through the open spaces 46 defined by the spokes 44, 52 and out through the outlet port 34. A secondary filter 62 is disposed in the chamber 56 over the primary filter 60. The filters 60, 62 maintain their position over the support structure 22 as they fit inside of and are secured in place by the manifold cap 16. This configuration insures that the waste materials passing through the manifold assembly 12 also pass through the filters 60, 62.

Referring to FIGS. 3 through 5, the connection 18 connects the housing 14 and cap 16 and retains them together. The connection 18 includes the shoulder 32 disposed on the exterior of the wall 24 about the open periphery 28 and a brim 74 disposed about the exterior of the skirt 66 and extending over and in spaced relationship to the ribs 70, 72. A lip 76 is disposed on the interior of the brim 74 for snapping over the shoulder 32 and retaining the housing 14 and cap 16 together. However, the connection 18 may be a molded hinge between the cap 16 and housing 14.

In one embodiment, the bottom 20 is conical and is disposed below the support surface 30. In addition, the wall 24 of the housing 14 and the skirt 66 are annular. The outer spokes 44 each include a polygonal web 48. Each web 48 extends axially downwardly from the filter support surface 30 to the conical bottom 20. Each web 48 further extends radially between the outer ring 40 and the passageway 36 and radially outwardly to the outer ring 40 and have radially inner edges 50 aligned with the passageway 36.

The lower edge 68 of the skirt 66 extends downwardly and is received in the groove 42. A plurality (three) of axially extending alignment ribs 70 are disposed on the exterior of the skirt 66 for engaging the interior of the wall 24 of the housing 14 and aligning the housing 14 and the cap 16 together. The alignment ribs 70 insure that the cap 16 is received properly within the housing 14 so that the lower edge 68 of the skirt 66 is correctly aligned with the groove 42 to compress the perimeter of each filter and secure the filters 60, 62 in place.

Additionally, a plurality (thirty-three) of axially extending sealing ribs 72 are disposed on the exterior of the skirt 66 for engaging the interior of the wall 24 of the housing 14 to provide a wedge fit. The brim 74 extends over and in spaced relationship to the ribs 70, 72, and the sealing ribs 72 seal the cap 16 within the housing 14 so that the manifold assembly 12 is water tight and remains water tight.

Figure 6:
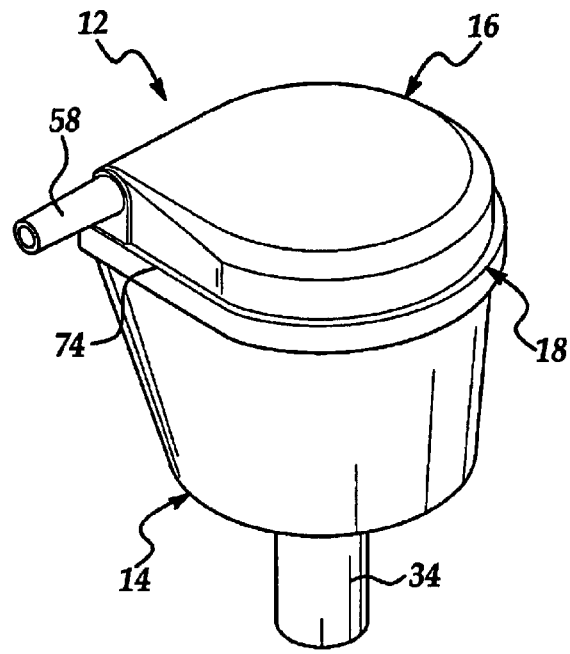
FIG. 6 is a perspective view of the manifold assembly according to another embodiment of the present invention.
Figure 7:
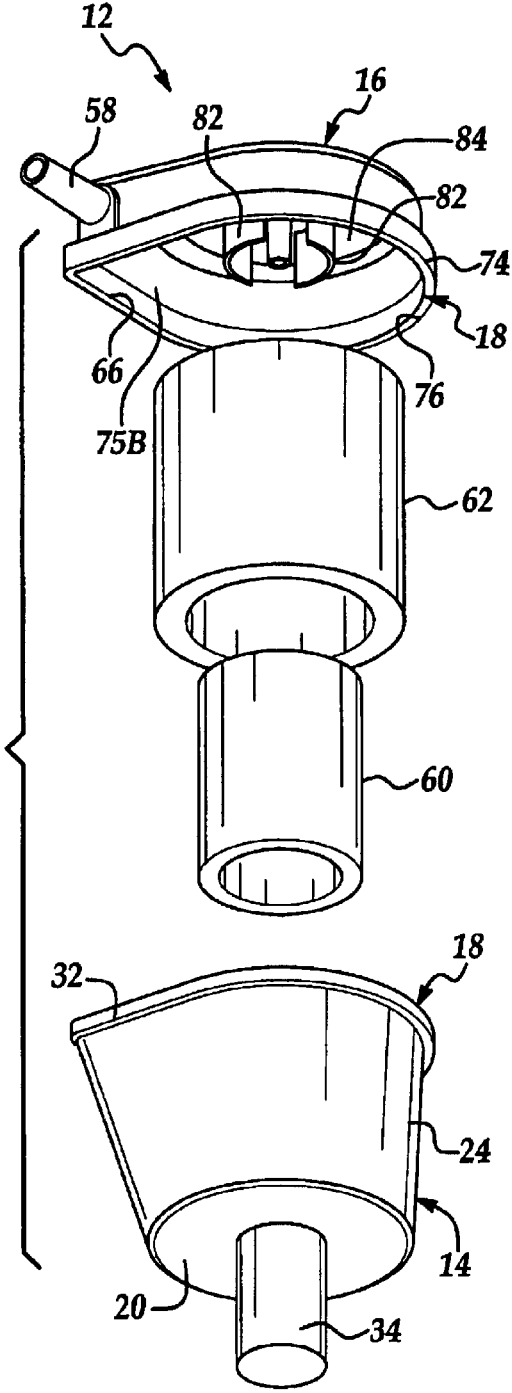
FIG. 7 is an exploded perspective view of the manifold assembly of FIG. 6.
Figure 8:
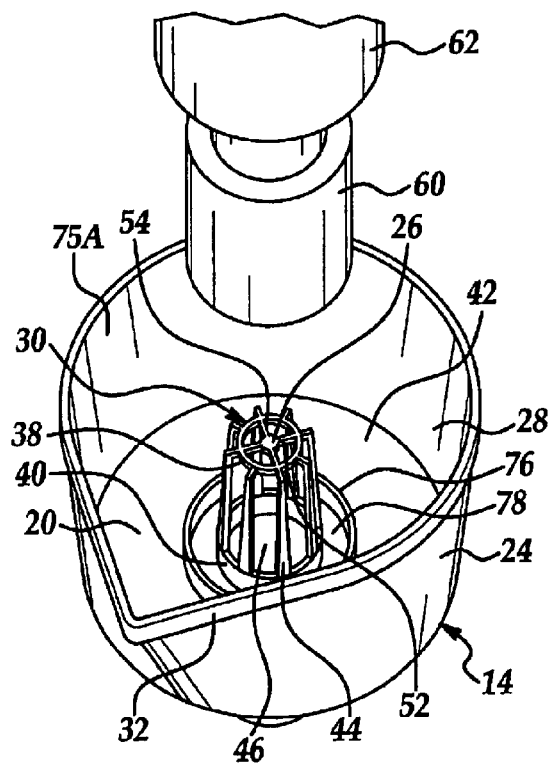
FIG. 8 is an exploded fragmentary view of the manifold assembly of FIG. 6.

In another embodiment, as shown in FIGS. 6 through 8, the filter support surface 30 extends upwardly from the bottom 20 for defining the plurality of open spaces 46. The primary and secondary filters 60, 62 are cylindrical and disposed over the upwardly extending support surface 30.

The intake port 58 is disposed on the cap 16 tangent to the wall 24 for receiving waste and forcing the waste against a first inner surface 75A of the housing 14 and a second inner surface 75B of the cap 16. The waste enters the chamber 56 and swirls inside the housing 14, thereby forcing the waste against the inner surfaces 75A, 75B to keep the filters 70, 72 clean longer.

An annular rib 76 is disposed in the groove 42 and spaced radially between the wall 24 and the outer ring 40 to define an inner groove 78 for receiving an end 80 of the primary filter 60. A plurality of engagement ribs 82 are disposed on an inner surface 84 of the cap 16 and extend outwardly therefrom into the chamber 56 for engaging the filters 60, 62. The engagement ribs 82 press the filters 60, 62 against the bottom 20 of the housing 14 to seal the filters 60, 62 within the annular rib 76 and prevent waste from passing beneath the filters 70, 72 and traveling to the outlet port 34.

The foregoing detailed description shows the preferred embodiments of the present invention are well suited to fulfill the objectives of the invention. It is recognized that those skilled in the art may make various modifications or additions to the preferred embodiments chosen herein to illustrate the present invention, without departing from the spirit of the present invention. Accordingly, it is to be understood that the subject matter sought to be afforded protection should be deemed to extend to the subject matter defined in the appended claims, including all equivalents thereof.

What is claimed is:

1. A manifold assembly for use in a medical waste collection device to direct fluid into the medical waste collection device while filtering material from the fluid, said assembly comprising:

a manifold housing having a bottom and a wall extending upwardly from said bottom about a first axis with said wall being cylindrically disposed about said first axis;

a support structure disposed on said bottom and including a plurality of outer spokes extending radially relative to said first axis toward said wall to define a filter support surface spaced from said bottom with a plurality of open spaces defined between adjacent spokes, an outer ring disposed on said bottom about said first axis and integral with outer ends of said plurality of spokes, said outer ring defining an imperforate annular groove with said bottom and said wall;

a primary filter supported by said filter support surface to filter the material from the fluid, said primary filter having a perimeter extending into said imperforate annular groove;

a manifold cap connected to said manifold housing to define a chamber therebetween, a skirt unitary with said cap and having a lower edge received in said imperforate annular groove to compress the perimeter of said primary filter and secure the primary filter in place;

an intake port disposed on said manifold cap about a second axis transverse to said first axis wherein said second axis is spaced from said filter support surface in said chamber such that the fluid entering said chamber changes direction between said intake port and said filter support surface; and an outlet port disposed on said manifold housing and extending downwardly therefrom about said first axis such that said outlet port is transversely oriented relative to said intake port.

2. An assembly as set forth in claim 1 including a secondary filter supported by said filter support surface and overlying said primary filter.

3. An assembly as set forth in claim 1 wherein said support structure includes an inner ring disposed about and spaced from said first axis and said outer spokes extend between said inner and outer rings.

4. An assembly as set forth in claim 3, further comprising a plurality of inner spokes extending between said first axis and said inner ring.

5. An assembly as set forth in claim 4 wherein said inner spokes are diametrically aligned in pairs to intersect at said first axis.

6. An assembly as set forth in claim 5 wherein each of said pairs of said inner spokes is aligned diametrically with a pair of said outer spokes.

7. An assembly as set forth in claim 1 wherein said outlet port defines a passageway extending into said chamber about said first axis and each of said outer spokes have inner edges aligned with said passageway.

8. An assembly as set forth in claim 1 wherein said manifold cap includes a top and said skirt depends from said top to a lower edge.

9. An assembly as set forth in claim 8 wherein said manifold housing includes a shoulder disposed on said wall.

10. An assembly as set forth in claim 9 including a brim disposed about said skirt and extending over and in spaced relationship to said skirt and a lip disposed on said brim for snap-fit engagement with said shoulder to connect said manifold cap to said manifold housing.

11. An assembly as set forth in claim 8 including a plurality of alignment ribs disposed on said skirt and engaging said wall of said manifold housing to align said manifold cap with said manifold housing.

12. An assembly as set forth in claim 11 including a plurality of sealing ribs spaced about said skirt and engaging said wall of said manifold housing to provide a snug fit between said manifold cap and said manifold housing.

13. An assembly as set forth in claim 1 wherein said bottom is disposed below said filter support surface in a conical shape.

14. An assembly as set forth in claim 13 wherein each of said outer spokes includes a polygonal web extending downwardly from said filter support surface to said conical bottom.

15. A manifold assembly for use in a medical waste collection device to direct fluid into the medical waste collection device while filtering material from the fluid, said assembly comprising:
   a manifold housing having an outlet port, a bottom, and a wall extending upwardly from said bottom about a first axis;
   a support structure disposed on said bottom and having a filter support surface spaced from said bottom to define a plurality of open spaces between said filter support surface and said bottom, said support structure including an inner ring disposed about and spaced from said first axis with a plurality of inner spokes extending radially between said first axis and said inner ring, and an outer ring disposed about and spaced from said inner ring with a plurality of outer spokes extending radially between said inner ring and said outer ring wherein each of said rings and said spokes have upper surfaces that are coplanar to define said filter support surface;
   a primary filter supported by said filter support surface to filter the material from the fluid; and
   a manifold cap connected to said manifold housing to define a chamber therebetween, said manifold cap including an intake port.

16. An assembly as set forth in claim 15 wherein said inner spokes are diametrically aligned in pairs to intersect at said first axis.

17. An assembly as set forth in claim 16 wherein each of said pairs of said inner spokes is aligned diametrically with a pair of said outer spokes.

18. An assembly as set forth in claim 15 wherein said intake port is disposed about a second axis transverse to said first axis.

19. An assembly as set forth in claim 18 wherein said outlet port is disposed on said bottom of said manifold housing and extends downwardly therefrom about said first axis.

20. An assembly as set forth in claim 19 wherein said outlet port defines a passageway extending into said chamber about said first axis and each of said outer spokes have inner edges aligned with said passageway.

21. An assembly as set forth in claim 15 wherein said manifold cap includes a top and a skirt depending from said top to a lower edge.

22. An assembly as set forth in claim 21 wherein said manifold housing includes a shoulder disposed on said wall.

23. An assembly as set forth in claim 22 including a brim disposed about said skirt and extending over and in spaced relationship to said skirt and a lip disposed on said brim for snap-fit engagement with said shoulder to connect said manifold cap to said manifold housing.

24. An assembly as set forth in claim 21 including a plurality of alignment ribs disposed on said skirt and engaging said wall of said manifold housing to align said manifold cap with said manifold housing.

25. An assembly as set forth in claim 24 including a plurality of sealing ribs spaced about said skirt and engaging said wall of said manifold housing to provide a snug fit between said manifold cap and said manifold housing.

26. An assembly as set forth in claim 15 wherein said bottom is disposed below said filter support surface in a conical shape.

27. An assembly as set forth in claim 26 wherein each of said outer spokes includes a polygonal web extending downwardly from said filter support surface to said conical bottom.

28. An assembly as set forth in claim 15 wherein said outer ring is spaced radially inward from said wall to define a groove therebetween.

29. An assembly as set forth in claim 28 wherein said manifold cap includes a top and a skirt depending from said top to a lower edge.

30. An assembly as set forth in claim 29 wherein said lower edge of said skirt is received in said groove and said lower edge engages a perimeter of said primary filter to compress said perimeter into said groove.

31. A manifold assembly for use in a medical waste collection device to direct fluid into the medical waste collection device while filtering material from the fluid, said assembly comprising:
   a manifold housing having a bottom and a wall extending upwardly from said bottom about a first axis;
   a support structure disposed on said bottom and having a filter support surface spaced from said bottom to define a plurality of open spaces between said filter support surface and said bottom, said support structure being spaced from said wall to define a groove therebetween;
   at least one filter supported by said filter support surface to filter the material from the fluid, each of said at least one filter having a perimeter;
   a manifold cap connected to said manifold housing to define a chamber therebetween;
   an intake port disposed on said manifold cap to direct the fluid into said chamber;

an outlet port disposed on said manifold housing; and a skirt unitary with said cap and having a lower edge wherein said lower edge compresses said perimeter of said at least one filter into said groove to prevent the fluid from bypassing said at least one filter as the fluid moves from said intake port to said outlet port.

32. A manifold assembly for use in a medical waste collection device to direct fluid into the medical waste collection device while filtering material from the fluid, said assembly comprising:

a manifold housing having a bottom and a wall extending upwardly from said bottom about a first axis;

a support structure disposed on said bottom and having a filter support surface spaced from said bottom to define a plurality of open spaces between said filter support surface and said bottom, said support structure being spaced from said wall to define a groove therebetween;

said support structure including an inner ring disposed about and spaced from said first axis with a plurality of inner spokes extending radially between said first axis and said inner ring, and an outer ring disposed about and spaced from said inner ring with a plurality of outer spokes extending radially between said inner ring and said outer ring wherein each of said rings and said spokes have upper surfaces that are coplanar to define said filter support surface;

at least two filters supported by said filter support surface to filter the material from the fluid, each of said at least two filters having a perimeter;

a manifold cap connected to said manifold housing to define a chamber therebetween with said manifold cap including a top and a skirt depending from said top to a lower edge wherein said lower edge compresses said perimeters of said at least two filters into said groove;

an intake port disposed on said manifold cap about a second axis transverse to said first axis wherein said second axis is spaced from said filter support surface in said chamber such that the fluid entering said chamber changes direction between said intake port and said filter support surface; and an outlet port disposed on said manifold housing and extending downwardly therefrom about said first axis such that said outlet port is transversely oriented relative to said intake port.

\* \* \* \* \*